United States Patent
Kennedy et al.

(10) Patent No.: US 6,365,171 B1
(45) Date of Patent: Apr. 2, 2002

(54) AMPHIPHILIC NETWORKS, IMPLANTABLE IMMUNOISOLATORY DEVICES AND METHODS OF PREPARATION

(75) Inventors: Joseph P. Kennedy, Akron, OH (US); Balazs Keszler, Budapest (HU); Györgyi Fenyvesi, Stow, OH (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 09/433,660

(22) Filed: Nov. 4, 1999

(51) Int. Cl.[7] .............................. A61F 13/00; A61K 9/14; A61K 47/30
(52) U.S. Cl. ........................ 424/422; 424/486; 424/487; 514/772.3; 514/866
(58) Field of Search ................................ 424/472, 486, 424/487, 422; 514/772.3, 866

(56) References Cited

U.S. PATENT DOCUMENTS

| | | | |
|---|---|---|---|
| 4,085,168 A | 4/1978 | Milkovich et al. | 260/886 |
| 4,486,572 A | 12/1984 | Kennedy | 525/283 |
| 4,942,204 A | 7/1990 | Kennedy | 525/293 |
| 5,073,381 A | 12/1991 | Ivan et al. | 424/487 |
| 5,158,881 A | 10/1992 | Aebischer et al. | 435/182 |
| 5,292,515 A | 3/1994 | Moro et al. | 424/422 |
| 5,800,828 A | 9/1998 | Dionne et al. | 424/422 |
| 5,807,944 A | 9/1998 | Hirt et al. | 526/279 |
| 5,834,001 A | 11/1998 | Dionne et al. | |
| 5,869,077 A | 2/1999 | Dionne et al. | 424/422 |
| 5,874,099 A | 2/1999 | Dionne et al. | 424/422 |

OTHER PUBLICATIONS

220th ACS Nat. Meeting Aug. 2000 Poly. 69 A. Domsan et al.*

Chen, D., Kennedy, J.P., Kory, M.M., and Ely, D.L. J. Biomed. Mater. Res., 23, 1327 (1989).

Faust, R. and Kennedy, J.P. J. Polym. Sci., Part A: Polym. Chem., 25, 1847 (1987).

Iván, B., Kennedy, J.P., and Chang, V.S.C. J. Polym. Sci. Polym. Chem., Ed. 18, 3177 (1980).

Iván, Bela, Kennedy, Joseph P., and Mackey, Paul W. Amphiphilic Networks III. Synthesis and Characterization of, and Drug Release from Poly (N, N–dimethylacrylamide)–1–polyisobutylene.

Kaszas, G., Puskas, J.E. and Kennedy, J.P. Macromolecules, vol. 25, pp. 1775–1779 (1992).

Kennedy, Joseph P., and Hiza, M. Polymer Bulletin, vol. 10, pp. 146–151 (1983).

Kennedy, Joseph P., and Keszler, Balazs. Journal of Macromolecular Science, Chemistry Edition, vol. A21, No. 3, pp. 319–334 (1984).

Keszler, B., Kennedy, J.P., and Mackey, P.W. Journal of Controlled Release, vol. 25, pp. 115–121 (1993).

(List continued on next page.)

Primary Examiner—James M. Spear
Assistant Examiner—Blessing Fubara
(74) Attorney, Agent, or Firm—Renner, Kenner, Greive, Bobak, Taylor & Weber

(57) ABSTRACT

The present invention provides high mechanical strength amphiphilic polymer networks and implantable biological devices that are capable of encasing and, thus, immunoisolating biological material from the immunological response of a host individual. The present invention also provides methods for the formation of the amphiphilic networks and implantable biological devices. The present invention also provides a method for the treatment of type I diabetes mellitus comprising the steps of encasing a sufficient amount of islet of Langerhans cells within said biological device, wherein said biological device is capable of immunoisolating said encased islet cells upon implantation into an individual; implanting said biological device into a diabetic host individual; allowing said implanted biological device to remain implanted said diabetic individual for a time sufficient to normalize the blood glucose level in said diabetic individual.

17 Claims, 5 Drawing Sheets

OTHER PUBLICATIONS

Keszler, B., Kennedy, J.P., Ziats, N.P., Brunstedt, M.R., Stack, S., Sun, J.K., and Anderson, J.M. Polym. Bull., 29, 68 (1992).

Mishra, M.K., Wang, B., and Kennedy, J.P. Polym. Bull., 17, 307 (1987).

Nagy, A., Faust, R., and Kennedy, J.P. Polym. Bull., 13, 97 (1985).

Park, D., Keszler, B., Galiatsatos, V., and Kennedy, J. P. J. Appl. Polym. Sci., vol. 66, 901 (1997).

Shamlou, S., Kennedy, J.P., and Levy, .R.L. "Amphiphilic Networks X. Diffusion of Glucose and Insulin (and Non-diffusion of Albumin) through Amphiphilic membranes" J. of Biomed. Mat. Res., 35(2), 165 (1997).

Sherman, M.A., and Kennedy, J.P. Journal of Polymer Science, Part A: Polymer Chemistry, 36, 1891 (1998).

Wilczek, L., and Kennedy, J.P. J. Polym. Sci., Part A: Polym. Chem., 25, 3255 (1987).

Joseph P. Kennedy and G. Caywood Richard, "Polyisobutylene–Toughened Poly(methyl methacrylate). Synthesis, Characterization, and Tensile Properties of PMMA–1–PIB Networks," Macromolecules, American Chemical Society (Washington, DC), vol. 26 (No. 4), p. 567–571, (Dec. 26, 1993).

* cited by examiner

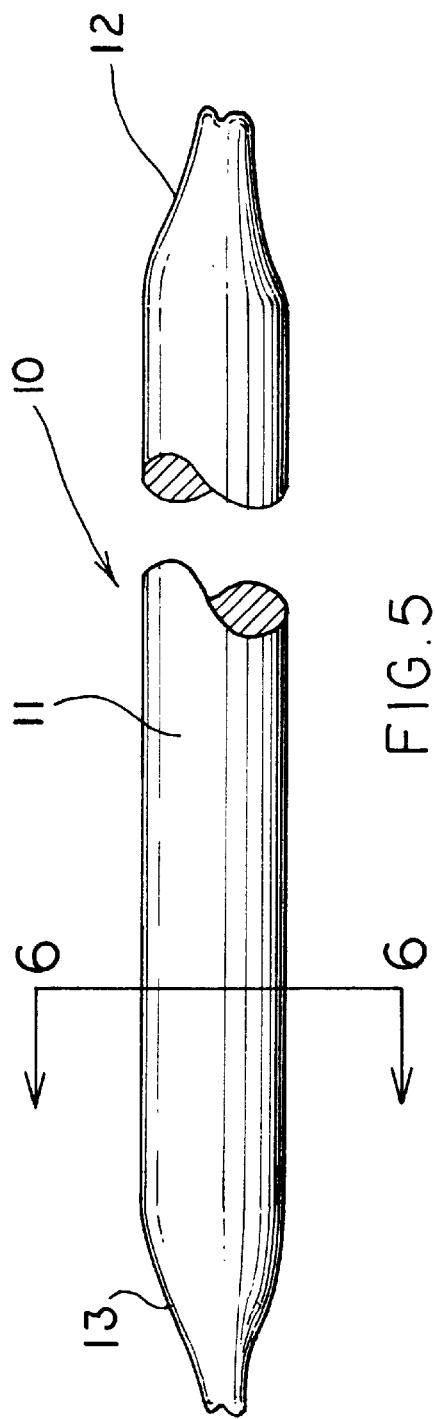
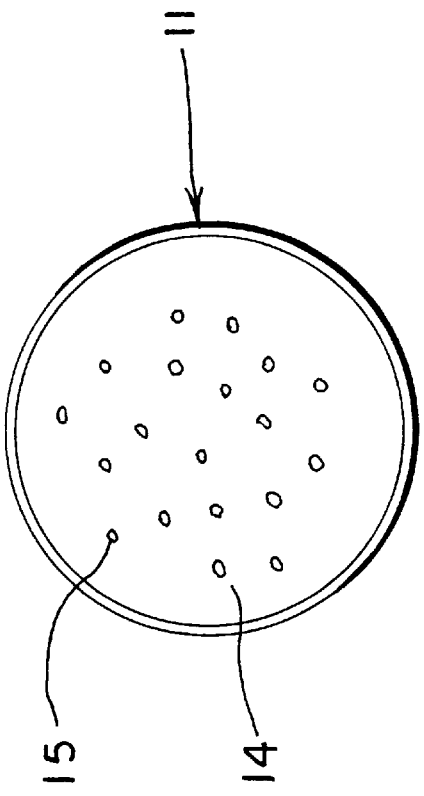

US 6,365,171 B1

AMPHIPHILIC NETWORKS, IMPLANTABLE IMMUNOISOLATORY DEVICES AND METHODS OF PREPARATION

The present invention was made in the course of research that was supported by National Science Foundation (NSF) Grant DMR-94-23202.

TECHNICAL FIELD OF THE INVENTION

The present invention is related to an amphiphilic polymer network comprising the reaction product of hydrophobic crosslinking agents and hydrophilic monomers and to methods for preparing the networks. The present invention is more particularly related to an amphiphilic polymer network comprising the reaction product of telechelic three-arm star polyisobutylene hydrophobic crosslinking agents and acrylate or methacrylate hydrophilic monomers, and implantable biological devices comprising the amphiphilic networks which are capable of encapsulating and immunoisolating biologically active moieties, such as cells, from the immune response of a host individual.

BACKGROUND OF THE INVENTION

Many medical deficiencies and diseases result from the inability of an individual's cells to produce normal biologically active moieties. Many of these deficiencies can be remedied by providing an exogenous source of needed biologically active moieties or pharmacological agents to the individual having the deficiency. A well known example of a disease that can be remedied by providing an exogenous source of a biological material or pharmacological agent is Type I diabetes mellitus, wherein the production of insulin by pancreatic Langerhans islets is substantially deficient, impaired or completely lost.

Encapsulation of human islet cells or tissues within a biologically compatible (biocompatible) device, such as a reservoir or physical barrier, followed by implantation of the device within an individual has been proposed to deliver biological material to an individual to treat Type I diabetes and other disease states. However, the immune response of the host, and consequently graft rejection of biological material, such as cells, tissues and organs has severely limited the use of implantation of such materials into individuals.

The supply of porcine pancreatic islet cells is much greater than human pancreatic islet cells and, therefore, a xenograft of porcine islet cells, if effectively immunoisolated from the normal immunological response of a human, would be of great benefit to a vast number of diabetic patients.

Amphiphilic polymer networks have been targeted as potential materials that are useful for implantation of biologically active moieties. An amphiphilic polymer network is a random assemblage of hydrophilic and hydrophobic polymer chains that is able to swell in both hydrophilic solvents (e.g., water) and hydrophobic solvents (e.g., a liquid hydrocarbon). Amphiphilic polymer networks have been disclosed in the prior art. U.S. Pat. Nos. 4,486,572 and 4,942,204 to Kennedy, U.S. Pat. No. 5,073,381 to Ivan, Kennedy and Mackey, and in Keszler and Kennedy, Journal of Macromolecular Science, Chemistry Edition, Vol. A21, No. 3, pages 319–334 (1984).

U.S. Pat. No. 4,486,572 to Kennedy discloses the synthesis of styryl-telechelic polyisobutylene and amphiphilic networks comprising the copolymerization product of the styryl-telechelic polyisobutylene with vinyl acetate or N-vinyl-2-pyrollidone.

U.S. Pat. No 4,942,204 to Kennedy discloses an amphiphilic copolymer network swellable in water or n-heptane but insoluble in either, comprising the product of the reaction of an acrylate or methacrylate of dialkylaminoalkyl with a hydrophobic bifunctional acryloyl or methacryloyl capped polyelofin. The preferred embodiment disclosed is an amphiphilic network having been synthesized by free-radical copolymerization of linear hydrophobic acrylate (A-PIB-A) or methacrylate (MA-PIB-MA) capped polyisobutylenes with 2-(dimethylamino)ethyl methacrylate (DMAEMA).

U.S. Pat. No. 5,073,381 to Ivan et al., a continuation-in-part of U.S. Pat. No. 4,942,204, discloses various amphiphilic copolymer networks that are swellable in water or n-heptane that comprise the reaction product of a hydrophobic linear acryloyl or methacryloyl capped polyolefin and a hydrophilic polyacrylate or polymethacrylate, such as N,N-dimethylacrylamide (DMAAm) and 2-hydroxyethyl methylmethacrylate (HEMA).

U.S. Pat. No. 4,085,168 to Milkovich et al. describes chemically joined, phase-separated self-cured hydrophilic thermoplastic graft copolymers which are copolymers of at least one hydrophilic (water soluble) ethylenically unsaturated monomer or mixture thereof and at least one copolymerizable hydrophobic macromolecular monomer having an end group which is copolymerizable with the hydrophilic monomer. The resulting copolymer is a graft copolymer characterized as having a comb-type structure consisting of a hydrophilic polymer backbone with hydrophobic polymer side chains bonded thereto. The side chains are disclosed as being bonded to the hydrophilic polymer at only one end of the side chain, so that no network results.

In addition, U.S. Pat. No. 5,807,944 to Hirt et al. discloses an amphiphilic segmented copolymer of controlled morphology comprising at least one oxygen permeable polymer segment and at least one ion permeable polymer segment, wherein the oxygen permeable segments and the ion permeable segments are linked together through a non-hydrolyzable bond. The oxygen permeable polymer segments are selected from polysiloxanes, perfluoroalkyl ethers, polysulfones, and other unsaturated polymers. The ion permeable polymers are selected from cyclic imino ethers, vinyl ethers, cyclic ethers, including epoxides, cyclic unsaturated ethers, N-substituted aziridines, β-lactones, β-lactanes, ketene acetales, vinyl acetates and phosphoranes.

U.S. Pat. No. 5,800,828 to Dionne et al. discloses immunoisolatory vehicles having a core and a surrounding jacket that is capable of secreting a biologically active product or of providing a biological function to a patient, said vehicle being permselective, biocompatible, and having a molecular weight cutoff permitting passage of molecules between the patient and the core of the vehicle, and wherein the jacket is selected from polyacrylonitrile-polyvinylchloride, polyacrylonitrile, poly(methyl methacrylate), poly(vinyl difluoride), polyolefins, polysulfones and celluloses.

The amphiphilic networks taught in the prior art, while suitable for biomedical applications, have tensile strengths that are rather low, namely less than or equal to about 0.5 MPa. It is therefore desirable in the art to develop amphiphilic networks, and implantable biological devices comprising the amphiphilic networks that have superior immunoisolatory properties, superior mechanical properties, and which are biocompatible, hemocompatible, and that exhibit excellent biostability when placed into a host individual for extended periods of time.

SUMMARY OF THE INVENTION

It is, therefore, an object of the present invention to provide an amphiphilic network.

It is another object of the present invention to provide an amphiphilic network, as above, that can encase biologically active moieties.

It is another object of the present invention to provide an amphiphilic network, as above, that is immunoisolatory, i.e., networks that can selectively regulate the passage of biological material into, out of, and through the network.

It is another object of the present invention to provide an amphiphilic network, as above, that is biocompatible with a host individual.

It is another object of the present invention to provide an amphiphilic network, as above, that exhibits excellent biostability once implanted into a host individual.

It is another object of the present invention to provide an amphiphilic network, as above, that is hemocompatible with a host individual.

It is another object of the present invention to provide an amphiphilic network, as above, that is readily sterilizable.

It is another object of the present invention to provide an amphiphilic network, as above, that is easily retrievable from a host individual after implantation in an individual.

It is another object of the present invention to provide an amphiphilic network, as above, that exhibits excellent mechanical properties.

It is another object of the present invention to provide an amphiphilic network, as above, that is swellable in both hydrophilic and hydrophobic solvents.

It is another object of the present invention to provide an implantable biological device that can encase biologically active substances and immunoisolate said biologically active substances from the immunological response of the host individual.

It is another object of the present invention to provide a method for the treatment of Type I diabetes mellitus.

These and other objects, together with the advantages thereof over the amphiphilic networks and biological devices comprising amphiphilic networks of the existing art, which shall become apparent from the specification which follows, are accomplished by the invention as hereinafter described and claimed.

In general, the present invention provides an amphiphilic network comprising the reaction product of hydrophobic crosslinking agents and hydrophilic monomers, wherein the hydrophobic crosslinking agents are tri-telechelic three-arm polyisobutylenes, having acrylate or methacrylate caps represented by formula (I);

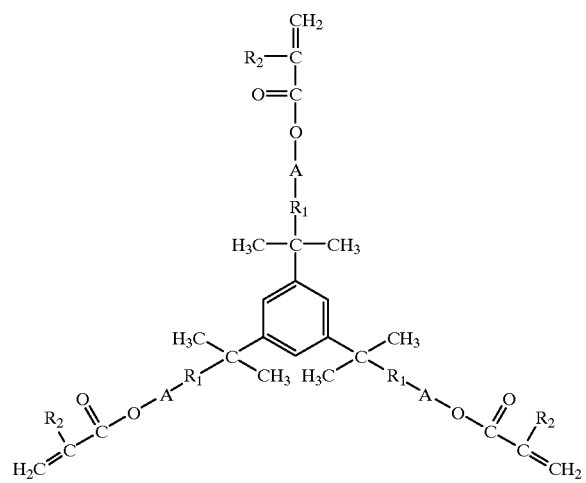

wherein $R_1$ is an isobutylene polymer represented by formula (II):

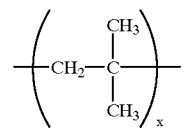

wherein x is the degree of polymerization of isobutylene and $R_2$ is hydrogen or a methyl group;

wherein A is a moiety that connects $R_1$ to the acrylate or methacrylate end caps;

and wherein the hydrophilic monomers are derived from an acrylate selected from the group consisting of formulas (II), (IV) and (V):

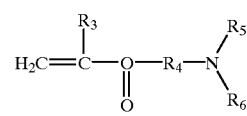

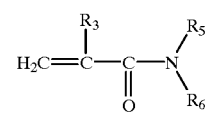

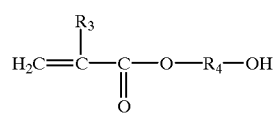

wherein $R_3$ is hydrogen or methyl, $R_4$ is an alkylene group having from about 2 to about 4 carbon atoms, and $R_5$ and $R_6$ may be the same or different and each is hydrogen or an alkyl radical having 1 to about 4 carbon atoms.

The present invention also provides a method of forming an amphiphilic network comprising the steps of:

copolymerizing and crosslinking hydrophilic monomers, wherein the hydrophilic monomers are derived from an acrylate selected from the group consisting of formulas (III), (IV) and (V):

(III)
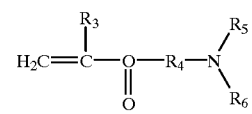

(IV)
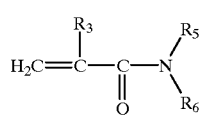

(V)
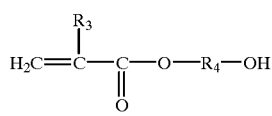

wherein $R_3$ is hydrogen or methyl, $R_4$ is an alkylene group having from about 2 to about 4 carbon atoms, and $R_5$ and $R_6$ may be the same or different and each is hydrogen or an alkyl radical having 1 to about 4 carbon atoms; and with hydrophobic crosslinking agents, wherein the hydrophobic crosslinking agents are three-arm star polyisobutylenes, having acrylate or methacrylate end caps represented by formula (I):

(I)
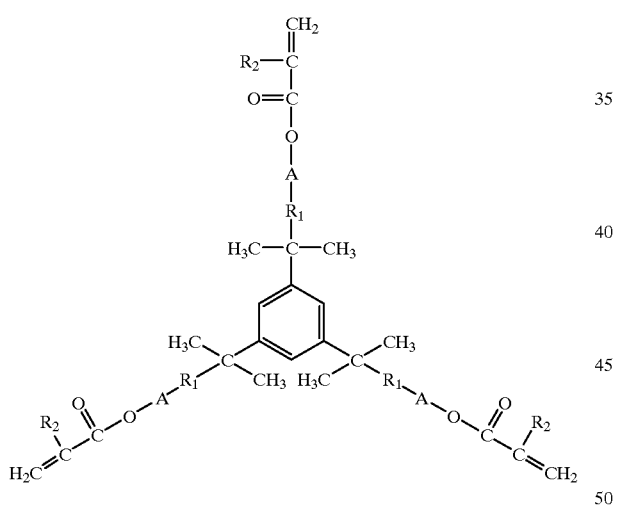

wherein $R_1$ is an isobutylene polymer represented by formula (II):

(II)
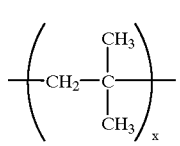

wherein A is a moiety that connects $R_1$ to the acrylate or methacrylate end caps;

wherein $R_2$ is hydrogen or a methyl group, and wherein x is the degree of polymerization of isobutylene.

The present invention further provides an implantable biological device that is capable of encapsulating biologically active moieties, and immunoisolating said moieties from the immunological response of a host individual, the device comprising an amphiphilic network comprising the reaction product of hydrophobic crosslinking agents and hydrophilic monomers, wherein the hydrophobic crosslinking agents are three-arm star polyisobutylenes, having acrylate or methacrylate end caps represented by formula (I):

(I)
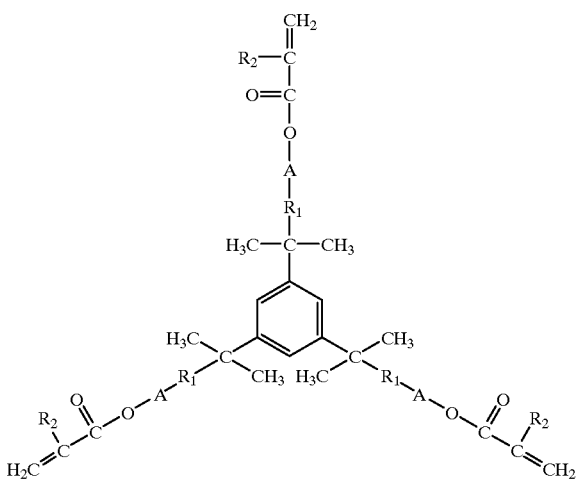

wherein $R_1$ is an isobutylene polymer represented by formula (II):

(II)
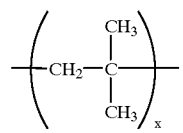

wherein A is a moiety that connects $R_1$ to the acrylate or methacrylate end caps;

wherein $R_2$ is hydrogen or a methyl group and wherein x is the degree of polymerization of isobutylene;

and wherein the hydrophilic monomers are derived from an acrylate selected from the group consisting of formulas (III), (IV) and (V):

(III)
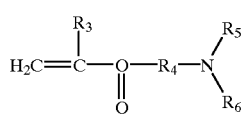

(IV)
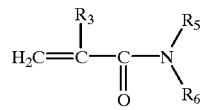

(V)
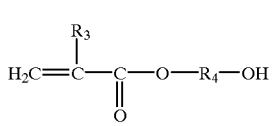

wherein $R_3$ is hydrogen or methyl, $R_4$ is an alkylene group having from about 2 to about 4 carbon atoms, and $R_5$ and $R_6$ may be the same or different and each is hydrogen or an alkyl radical having 1 to about 4 carbon atoms.

The present invention further provides a method for the production of an implantable biological device, the device capable of encasing and immunoisolating biologically active moieties upon implantation into a host individual, comprising the steps of forming an amphiphilic network comprising the reaction product of hydrophobic crosslinking agents and hydrophilic monomers, wherein the hydrophobic crosslinking agents are three-arm star polyisobutylenes, having acrylate or methacrylate end caps represented by formula (I):

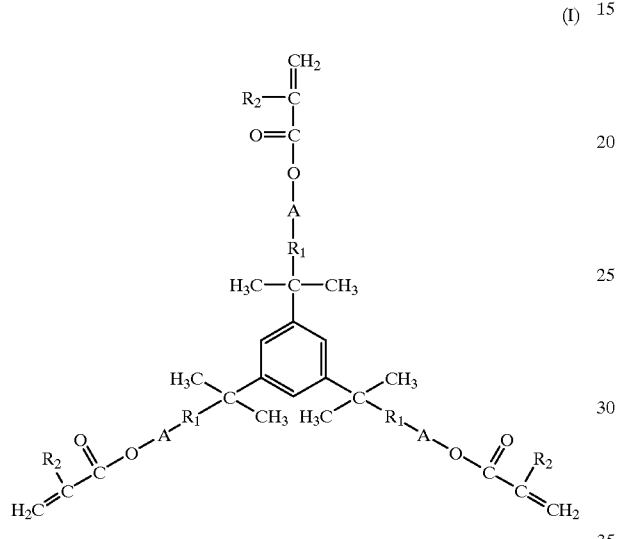

(I)

wherein $R_1$ is an isobutylene polymer represented by formula (II):

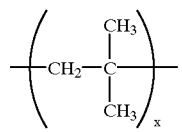

(II)

wherein A is a moiety that connects $R_1$ to the acrylate or methacrylate end caps;

wherein $R_2$ is hydrogen or a methyl group and wherein x is the degree of polymerization of isobutylene;

and wherein the hydrophilic monomers are derived from an acrylate selected from the group consisting of formulas (III), (IV) and (V):

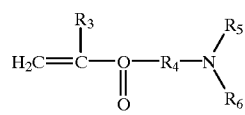

(III)

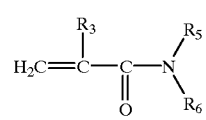

(IV)

-continued

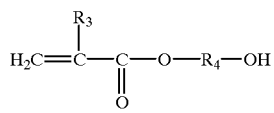

(V)

wherein $R_3$ is hydrogen or methyl, $R_4$ is an alkylene group having from about 2 to about 4 carbon atoms, and $R_5$ and $R_6$ may be the same or different and each is hydrogen or an alkyl radical having 1 to about 4 carbon atoms; and forming said amphiphilic network into a desired three-dimensional geometric shape.

The present invention further provides a method for treating Type I diabetes in a diabetic host individual comprising the steps of providing an amphiphilic network comprising the reaction product of hydrophobic crosslinking agents and hydrophilic monomers, wherein the hydrophobic crosslinking agents are three-arm star polyisobutylenes, having acrylate or methacrylate end caps represented by formula (I);

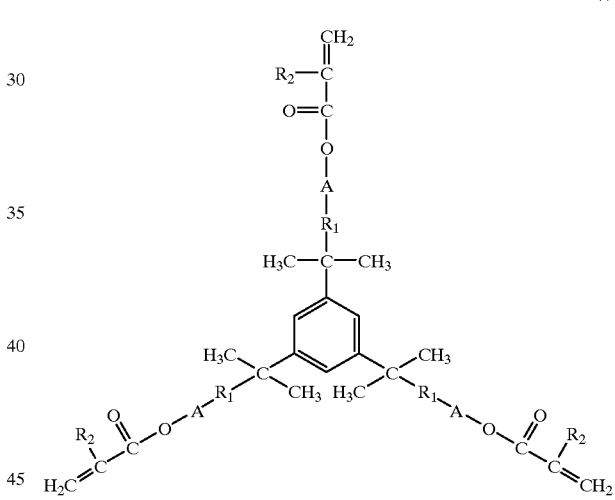

(I)

wherein $R_1$ is an isobutylene polymer represented by formula (II):

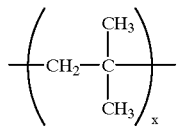

(II)

wherein A is a moiety that connects $R_1$ to the acrylate or methacrylate end caps;

wherein $R_2$ is hydrogen or a methyl group and wherein x is the degree of polymerization of isobutylene;

and wherein the hydrophilic monomers are derived from an acrylate selected from the group consisting of formulas (III), (IV) and (V):

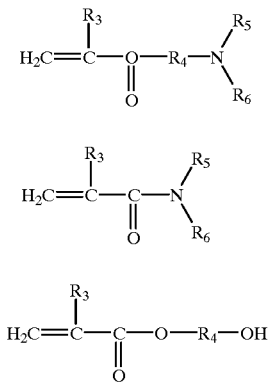

wherein $R_3$ is hydrogen or methyl, $R_4$ is an alkylene group having from about 2 to about 4 carbon atoms, and $R_5$ and $R_6$ may be the same or different and each is hydrogen or an alkyl radical having 1 to about 4 carbon atoms; forming the amphiphilic network into an elongated tubular device; encasing a sufficient amount of pancreatic islet of Langerhans cells within the tubular device, wherein the tubular device is capable of immunoisolating the encased islet cells upon implantation into an individual; implanting the tubular device into a diabetic host individual; allowing the implanted tubular device to remain implanted in the diabetic individual for a time sufficient to normalize the blood/glucose level in the diabetic individual.

BRIEF DESCRIPTION OF THE DRAWINGS

FIG. 5 is a schematic representation of an implantable tubular biological device prepared from the amphiphilic polymer networks of the present invention.

FIG. 6 is a schematic representation of a cross section of an implantable tubular biological device of the present invention depicting biologically active moieties encased within an amphiphilic network.

DETAILED DESCRIPTION OF THE INVENTION

Figure 1:
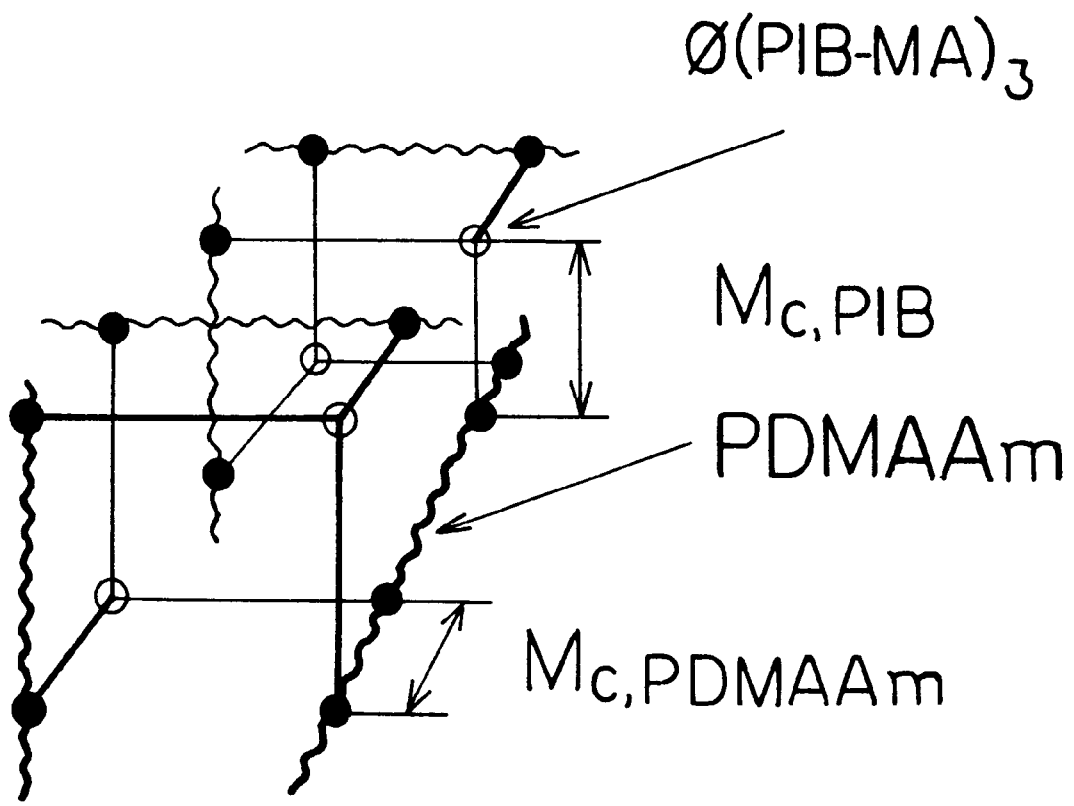
FIG. 1 is a schematic representation of the amphiphilic network of the present invention based on three-arm star methacryoyl-capped polyisobutylene (Ø(PIB-MA)$_3$).

Amphiphilic networks based on the reaction product of hydrophobic acrylate-capped and/or methacrylate-capped tri-telechelic three-arm star polyisobutylene crosslinking agents and hydrophilic polyacrylates or polymethacrylates have been synthesized. The amphiphilic networks of the present invention are characterized by two molecular weights ($M_c$s) between crosslinking points, and have homogenous and heterogenous crosslink points. The amphiphilic networks swell in both water and n-heptane, which demonstrates a cocontinuous hydrophobic-hydrophilic microarchitecture. Water-swollen amphiphilic networks of the present invention exhibit superior mechanical properties, such as greater tensile strength and elongation, as compared to the amphiphilic networks of the prior art. Implantable immunoisolatory biological devices comprising the amphiphilic networks of the present invention are biocompatible, hemocompatible, sterilizible, exhibit excellent biostability, and are easily retrievable from a host individual after implantation.

To assist with the understanding of the present invention, a glossary of terms and definitions that are used throughout the specification are provided below.

The term "individual", as used throughout this specification, refers to a human or animal subject.

The phrase "biologically active moiety or moieties", as used throughout this specification, refers to any biological material, biological substance, or pharmacological agent that can alter, modify or elicit a physiological response from the host individual. Preferred examples of biologically active moieties are described hereinbelow in the detailed description of the invention.

The term "immunoisolatory", as used throughout this specification, refers to the capability of the amphiphilic polymer networks and implantable biological devices of the present invention to isolate or otherwise protect implanted biologically active moieties from the immunological response of a host individual. The term "immunoisolatory" can also refer to the ability of the amphiphilic network to selectively regulate the passage of molecules across the network.

The term "biocompatible", as used throughout this specification, refers to the capability of the amphiphilic polymer networks and implantable biological devices of the present invention to avoid eliciting a detrimental physiological response from the host individual after implantation, such that the implanted network or device is not rejected by the host individual.

The term "biostability", as used throughout this specification, refers to the capability of the amphiphilic polymer networks and implantable biological devices of the present invention to resist or otherwise withstand the protective physiological responses of the host individual, thus allowing the implanted network and/or device to remain implanted and functional in the host individual for a desired period of time.

The term "hemocompatible", as used throughout this specification, refers to the capability of the amphiphilic networks and biological devices of the present invention to avoid eliciting a detrimental response from the blood of the host individual.

The phrase "homogenous crosslink points", as used throughout this specification, refers to crosslink points connecting only hydrophobic monomer segments in the amphiphilic polymer networks of the present invention. The "homogenous crosslink points" are located at the core of the telechelic three-arm star hydrophobic crosslinking agent.

The phrase "heterogenous crosslink points", as used throughout this specification, refers to crosslink points connecting hydrophobic monomers to hydrophilic monomers in the amphiphilic polymer networks of the present invention.

The term "$M_{n\ hydrophobic}$", as used throughout this specification, refers to the number average molecular weight of the hydrophobic moieties employed in the amphiphilic polymer networks of the present invention.

The term "$M_{n\ hydrophilic}$", as used throughout this specification, refers to the number average molecular weight of the hydrophilic moieties employed in the amphiphilic polymer networks of the present invention.

The abbreviation "$M_{c\ hydrophobic}$", as used throughout this specification, refers to the molecular weight of the hydrophobic crosslinking segments between homogenous and heterogenous crosslink points in the amphiphilic polymer networks of the present invention.

The abbreviation $M_{c\ hydrophilic}$, as used throughout this specification, refers to the calculated molecular weight of the hydrophilic monomer segments between two heterogenous crosslink points in the amphiphilic polymer networks of the present invention.

The present invention will be further described with reference to the synthesis and amphiphilic polymer networks from methacrylate-capped three-arm star polyisobutylenes (Ø(PIB-MA)$_3$) and polyacrylates such as N,N-dimethylacrylamide (DMAAm), 2-(dimethylamino)ethyl methacrylate (DMAEMA) and 2-hydroxyethyl methylmethacrylate (HEMA). A preferred amphiphilic polymer network is synthesized from Ø(PIB-MA)$_3$ and DMAAm.

The starting materials for preparation of amphiphilic networks of this invention are (a) tri-telechelic three-arm star hydrophobic acrylate or methacrylate-capped polyisobutylene crosslinking agents and (b) a hydrophilic ω(dialkylamino) lower alkyl acrylate or methacrylate or a hydrophilic dialkyl acrylamide or methacrylamide or a hydrophilic ω-hydroxy alkyl acrylate or methacrylate monomers.

The hydrophobic acrylate-capped or methacrylate-capped polyisobutylene is trifunctional (tri-telechelic), and may be represented by the following formula (I):

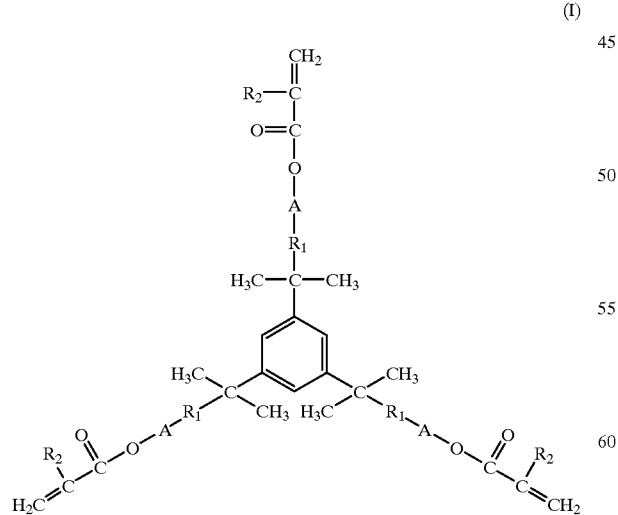

(I)

wherein $R_1$ is an isobutylene polymer represented by formula (II):

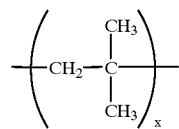

(II)

wherein A is a moiety that connects $R_1$ to the acrylate or methacrylate end caps; and wherein $R_2$ is hydrogen or methyl and wherein x is the degree of polymerization of the isobutylene.

The hydrophobic crosslinking agents (I) are three-arm star polyisobutylenes having a number average molecular weight $M_n$ of at least about 500, preferably from about 2,000 to about 50,000, more preferably from about 4,000 to about 15,000; a degree of polymerization x corresponding to this $M_n$ (i.e, x is preferably from about 35 to about 100) and a molecular weight distribution $M_w/M_n$ preferably from about 3.0 to about 1.1; capped at both ends with acrylate or methacrylate groups. Synthesis of the preferred macromonomer (I), i.e., methacryloyl-capped polyisobutylene is described in J. P. Kennedy and M. Hiza, Polymer Bulletin. Vol. 10, pages 146–151 (1983).

Moiety A can be any moiety which can connect $R_1$ to the acrylate or methacrylate end caps on each arm of the three arm star polyisobutylene crosslinking agent. Suitable moieties that can comprise moiety A include, but are not limited to moieties represented by formulas (VI) and (VII):

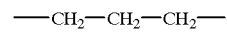

(VI)

and

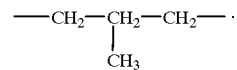

(VII)

The hydrophilic comonomers are derived from a monofunctional monomer or mixture thereof that is copolymerizable with the acrylate or methacrylate end groups of the hydrophobic acrylate or methacrylate-capped three arm star polyisobutylene, and which yields a water soluble segment when homopolymerized. Preferred hydrophilic polyacrylate segments are those derived from acrylate monomer of formulas (III), (IV), and (V) as shown below:

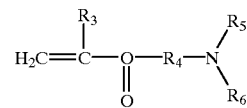

(III)

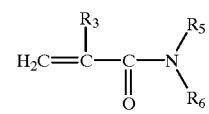

(IV)

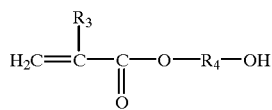

(V)

where $R_3$ is hydrogen or methyl, $R_4$ is an alkylene group of 2 to about 4 carbon atoms, and $R_5$ and $R_6$ may be the same or different and each is hydrogen or an alkyl radical having from about 1 to about 4 carbon atoms.

The preferred acrylate of the formula (III) is 2-(dimethylamino)ethyl methacrylate (DMAEMA). The preferred acrylates of formulas (IV) and (V) for controlled and/or sustained drug release networks are N,N-dimethylacrylamide (DMAAm) and 2-hydroxyethyl methacrylate (HEMA), respectively. Other suitable hydrophilic comonomers include N-vinyl pyrrolidone, acrylamide and other similar hydrophilic acrylates or methacrylates.

Preferably the hydrophobic crosslinking agent (I) and the hydrophilic comonomer have the same ester group, which is preferably methacrylate, so that the amphiphilic polymer network which is formed will be a random copolymer.

The weight ratio of the hydrophilic monomer to the hydrophilic comonomer is in the range of about 80:20 weight percent to about 20:80 weight percent, preferably in the range of about 70:30 weight percent to about 30:70 weight percent, and more preferably in the range of about 60:40 weight percent to about 40:60 weight percent, and most preferably in the range of about 50:50 weight percent.

When the reaction of the hydrophobic and hydrophilic monomers is complete, the reaction product may be extracted sequentially with a non-polar solvent such as n-hexane, a polar organic solvent such as methanol, and water to remove the unreacted hydrophobic crosslinker, for example Ø(PIB-MA)$_3$, unreacted hydrophilic comonomer, for example DMAAm, and the hydrophilic homopolymer, for example PDMAEMA. This leaves the amphiphilic network of the present invention.

A schematic representation of the novel amphiphilic polymer networks of the presented invention based on three-arm star Ø(PIB-MA)$_3$ is shown in FIG. 1. The straight lines represent the hydrophobic Ø(PIB-MA)$_3$ segments, the wavy lines represent the hydrophilic polyacrylate segments. The "open" circles represent homogenous crosslink points, and the darkened circles represent heterogenous crosslink points. As can be seen from FIG. 1, the amphiphilic polymer networks of the present invention have two types of crosslink points, namely homogenous crosslink points and heterogenous crosslink points, and are characterized by two $M_c$s. The core of the Ø(PIB-MA)$_3$ segments is a homogenous crosslink point, only crosslinking hydrophobic segments. The incorporation of the Ø(PIB-MA)$_3$ into the growing hydrophiphilic PDMAAm segments creates the heterogenous crosslink points, which connect the hydrophilic segments to the hydrophobic segments. $M_{c, PIB}$ is the molecular weight of one arm of the three-arm star polyisobutylene segment between crosslink points, and $M_{c, PDMAAm}$ is the molecular weight of the hydrophilic PDMAAm segment between two heterogneous crosslink points.

Assuming complete incorporation of the Ø(PIB-MA)$_3$ into the growing PDMAAm chains, the $M_{c, PDMAAm}$ and the crosslink density of the amphiphilic polymer network can be calculated from the overall composition of and the molecular weight of the polyisobutylene as follows:

$$M_{c,PDMAAm} = \frac{M_{n,DMAAm}}{3X} = \frac{M_{n,PIB} PDMAAm\%}{3PIB\%}$$

where $M_{n, DMAAm}$ is the molecular weight of the DMAAm monomer, X is the crosslink concentration (i.e.-mol crosslinker/mol monomer), and 3 is the functionality of the Ø(PIB-MA)$_3$, $M_{n, PIB}$ is the molecular weight of the polyisobutylene (PIB), and PDMAAm % and PIB % are the weight percents of the hydrophilic PDMAAm and PIB in the amphiphilic network, respectively.

Table I, hereinbelow, shows the data for various amphiphilic polymer networks of the present invention.

TABLE I

| Example No. | Network | Feed Composition | | Hexane Extract % | Methanol Extract % | Network Composition | | $M_{c, PDMAAm}$ g/mol | Crosslink Density mol/g × 10$^4$ |
| | | Ø(PIB-MA)$_3$ g | DMAAm g | | | PIB(MA)$_3$ % | DMAAm % | | |
| --- | --- | --- | --- | --- | --- | --- | --- | --- | --- |
| 1 | A-4.5-30 | 0.0600 | 0.1400 | 2.41 | 4.31 | 30 | 70 | 3500 | 2.67 |
| 2 | A-4.5-40 | 0.0800 | 0.1200 | 3.82 | 3.80 | 40 | 60 | 2250 | 3.56 |
| 3 | A-4.5-50 | 0.1000 | 0.1000 | 4.25 | 2.59 | 50 | 50 | 1500 | 4.44 |
| 4 | A-4.5-60 | 0.1200 | 0.0800 | 4.60 | 1.28 | 59 | 41 | 1040 | 5.24 |
| 5 | A-10-30 | 0.0600 | 0.1400 | 2.52 | 5.48 | 31 | 69 | 7420 | 1.24 |
| 6 | A-10-40 | 0.0800 | 0.1200 | 4.37 | 5.27 | 40 | 60 | 5000 | 1.60 |
| 7 | A-10-50 | 0.1000 | 0.1000 | 5.10 | 4.63 | 50 | 50 | 3330 | 2.00 |
| 8 | A-10-60 | 0.1200 | 0.0800 | 5.70 | 2.19 | 59 | 41 | 2320 | 2.36 |
| 9 | A-15-30 | 0.0600 | 0.1400 | 3.65 | 7.88 | 31 | 69 | 11130 | 0.83 |
| 10 | A-15-40 | 0.0800 | 0.1200 | 5.18 | 7.15 | 41 | 59 | 7200 | 1.09 |
| 11 | A-15-50 | 0.1000 | 0.1000 | 6.35 | 5.59 | 50 | 50 | 5000 | 1.33 |
| 12 | A-15-60 | 0.1200 | 0.0800 | 7.43 | 4.20 | 59 | 41 | 3470 | 1.57 |

As can be seen from Table I, the crosslink density of the amphiphilic networks of the present invention is from about 0.8×10$^4$ mol/g to about 5.24×10$^4$ mol/g. The crosslink density of the amphiphilic network, however, is dependent on the composition of the network. While the $M_{c, PDMAAm}$ decreases with increasing polyisobutylene (PIB) content and increases with increasing polyisobutylene molecular weight, the crosslink density increases with increasing polyisobutylene content and decreases with increasing polyisobutylene molecular weight. Thus, amphiphilic networks based on three-arm star Ø(PIB-MA)$_3$ have a lower $M_{c\ PDMAAm}$ and a higher crosslink density as compared to amphiphilic polymer networks based on linear bifunctional acryloyl-capped or methacryloyl-capped polyolefins, such as bifunctional methacryloyl-capped polyisobutylene (MA-PIB-MA).

Amphiphilic polymer networks of the present invention are swellable in both polar solvents such as water, and non-polar solvents such as n-heptane, but are not soluble in either. Solvent swelling of the amphiphilic networks of the present invention is in the range of about 30% to about 180% in water (i.e., polar solvents), and is in the range of about 5% to about 100% in n-heptane (i.e., non-polar solvents).

Although the present invention has been described with particular reference to amphiphilic networks comprising the reaction product of telechelic three-arm star Ø(PIB)$_3$ and hydrophilic DMAAm, other networks according to the present invention in which the hydrophilic polymer chains are based on a monomer other than DMAAm, exhibit similar swellability in both water and n-heptane as the preferred amphiphilic network.

The tensile strength of the amphiphilic polymer networks of the present invention in the dry state is from about 5 to about 7 MPa. The tensile strength of water-swollen (wet state) amphiphilic networks is from about 0.5 to about 1 MPa. By way of illustration, but not in limitation, the tensile strength of an amphiphilic polymer network comprising Ø(PIB-MA)$_3$ and poly-DMAAm (PDMAAm) in either the wet or dry state is at least about 0.8 Mpa. The tensile strength of the amphiphilic networks in the dry state may be from about 0.9 to about 8 MPa, and the tensile strength of an water-swollen (wet state) amphiphilic polymer network comprising Ø(PIB-MA)$_3$ and poly-DMAAm (PDMAAm) may be from about 0.8 to about 1 MPa.

As discussed hereinabove, the present invention also provides implantable biological devices that are capable of encapsulating biologically active moieties, and immunoisolating said moieties from the immunological response of a host individual that comprise the swellable amphiphilic polymer networks of the present invention.

In order for the biological device of the present invention to encase and immunoisolate biologically active cells and substances, the amphiphilic polymer network of the present invention is typically formed into a desired three-dimensional structure. The biological device having a three-dimensional structure, is constructed to have a particular volume for encasing and immunoisolating biologically active cells and substances.

Although any size, shape, configuration or structure can be employed, it is preferred that the size, shape, or configuration of the biological device be such that it will allow as non-invasive a medical procedure as possible to implant the device in a host individual. A preferred geometric structure comprises an elongated cylindrical or tubular structure having opposing ends adapted to be sealed, thus capable of forming an implantable biological device having an inner volume for encasing and immunoisolating biologically active cells and substances. With reference to FIG. 5, the preferred tubular biological device (10) comprising the amphiphilic network (11) of the present invention is shown. The opposing ends (12,13) of the tubular biological device are pinched to seal the inner volume. The opposing ends (12,13) can be sealed using an adhesive, such as cyanoacrylate and the like. With reference to FIG. 6, a cross section of tubular biological device (10) shows the device comprising the amphiphilic network (11) of the present invention. The inner volume of the tubular device (10) contains a desired amount of biologically active moieties (15), such as islet cells. The inner volume of the tubular device (10) may also contain a matrix (14), such as an alginate matrix, to prevent the aggregation of the moieties within the inner volume of the tubular device (10).

The thickness of the amphiphilic membrane of a tubular shaped biological device is preferably from about 0.001 centimeters to about 0.1 centimeters, more preferably from about 0.003 centimeters to about 0.08 centimeters, and most preferably form about 0.005 centimeters to about 0.02 centimeters thick.

The length of a tubular shaped biological device comprising the amphiphilic networks described hereinabove is from about 1 to about 50 centimeters, preferably less than about 20 centimeters in length, more preferably less than about 10 centimeters in length, and most preferably from about 2 centimeters to about 5 centimeters in length.

The inner volume of a 4 centimeter (cm) long tubular biological device of the present invention is preferably less than about 0.1 milliliters.

The outer diameter of a tubular shaped biological device comprising the amphiphilic networks described hereinabove is preferably less than about 3 millimeters, more preferably less than about 2 millimeters, and most preferably less than about 1 millimeter.

The present invention also provides a method of forming an amphiphilic network that is swellable in water and n-heptane. The process for forming the amphiphilic network is accomplished copolymerizing and crosslinking hydrophilic monomers with hydrophobic acryloyl or methacryoyl-capped polyisobutylene monomers, such as methacrylate-capped three arm star tri-telechelic polyisobutylene Ø(PIB-MA)$_3$.

In one preferred embodiment, implantable thin-walled tubular amphiphilic networks suitable for encasing and immunoisolating biological matter are formed by simultaneous free radical copolymerization in a horizontally disposed rotating glass tube in a thermostatted oven. The glass reactor tube is generally characterized as having a length of about 20 to about 25 centimeters and an inner diameter of about 0.05 to about 2 millimeters. The simultaneous free radical copolymerization and crosslinking is carried out in a suitable organic solvent, such as tetrahydrofuran (THF) and a suitable initiator, such as azobisisobutyronotrile (AIBN). The glass tube is sealed under nitrogen, and rotated at about 200 to about 400 RPM at a temperature of about 60° C. to about 65° C. The centrifugal force moves the active charge to the wall of the rotating tube. The reaction is carried out for up to about 2 days. The glass reactor tube is opened, and the tubular amphiphilic network is removed from the glass tube, and washed sequentially with hexanes, alcohol and water each for 24 hours at room temperature.

The implantable biological devices comprising the amphiphilic networks of the present invention are capable of encasing biologically active moieties and immunisolating the encased moieties from the immunological response of the host individual after implantation.

The term "permeability", as used throughout this specification, refers to the ability of molecules of a certain size to pass into or out of the amphiphilic tubular networks of the present invention. Thus, increasing the permeability of the polymer network refers to the ability of the polymer network to allow the passage of larger molecules through or across the device. Decreasing the permeability of the polymer network refers to the ability of the polymer network to restrict the passage of a certain size molecules through or across the device. The amphiphilic networks of the present invention should prevent the passage of molecules having a molecular weight greater than about 80,000 daltons, preferably the amphiphilic networks of the present invention should prevent the passage of molecules having a molecular weight greater than about 70,000 daltons, and more preferably amphiphilic networks of the present invention should prevent the passage of molecules having a molecular weight greater than about 40,000 daltons. It should be noted that the amphiphilic networks of the present invention can be prepared to exclude molecules smaller that 40,000 daltons. The implantable biological devices are designed to allow the rapid passage (diffusion) of molecules, such as insulin, glucose, oxygen, carbon dioxide, salts and water, while restricting the passage of larger molecules, such as immunoglobulins.

The amphiphilic polymer networks of the present invention are hydrogels which, in the hydrated state, are similar to natural tissue. As a result of this characteristic, the amphiphilic polymer networks and biological devices prepared from the networks have broad range of biomedical applications. The amphiphilic polymer networks and biological devices prepared from the networks may be used in biomedical applications including, but not limited to, implantable biological devices for encasing biologically active cells and substances, implantable biological devices for immunoisolating encased biologically active moieties from the immune response of an individual, controlled drug release, implants for enzyme immobilization, artificial arteries, blood-contacting applications, various implantable reservoirs for a pharmacologically active agent, in human and veterinary applications. Biologically active moieties include, but are not limited to, cells, tissue, hormones, enzymes, growth factors, and erythropoietin.

Without limiting the present invention in any manner, the preferred biologically active moiety are pancreatric Lagerhans islet that will be used to normalized the blood/glucose level in an individual suffering from Type I diabetes.

In one preferred embodiment of the present invention, essentially water soluble sodium alginate is introduced into the inner volume of the implantable biological device along with biologically active moieties. The biological device is then placed into a solution of calcium chloride. Preferably, the calcium chloride solution is a 2.0 weight percent aqueous solution of calcium chloride. The calcium chloride penetrates the amphiphilic network into the biolgical device to crosslink the sodium alginate. The crosslinked sodium alginate forms a loose gel which substantially prevents aggregation of the moieties within the biological device. It is important to note that the addition of the crosslinked alginate matrix to the inner volume of the biological device of the present invention does not effect the permeability or immunoisolatory properties of the amphiphilic polymer networks.

Pharmacologically active agents are any agent or combination of agents which cause, suppress, modify, alter or otherwise cause an in vivo physiological response. Suitable pharmacologically active agents that may be encased within the inner volume of the biological devices of the present invention include, but are not limited to, insulin, antifungal agents, antibacterial agents, anti-viral agents, growth factors and hormones.

As mentioned hereinabove, the present invention provides a method for treating Type I diabetes. The treatment involves providing the amphiphilic network of the present invention. The amphiphilic network is formed into an elongated tubular device that can be implanted into a diabetic host individual. A sufficient amount of pancreatic beta cells are encased within said tubular biological device. The biological device containing the pancreatic beta cells is then implanted into a diabetic individual. The implanted biological device is allowed to remain implanted in the host diabetic individual for a time sufficient to normalize the blood/glucose level in the diabetic individual.

It is important to note that implantable biological devices prepared from the amphiphilic networks described herein are capable of immunoisolating the encased biologically active cells from the immune response of the diabetic individual. The tubular biological device allows passage of glucose into the device to stimulate production of insulin by the encased cells. The biological device allows passage of the insulin produced by the encased cells out of the device.

With respect to the treatment of Type I diabetes, it has been found that preferably about 700,000 to about 1,000,000 pancreatic islet cells are required to normalize, to about 100 mg/ml, the blood glucose level of an 80 kilogram human, thus reversing the effects of diabetes in an individual. This determination is generally based on the assumption that about 10,000 pancreatic islet cells per kilogram of body weight is desirable. Accordingly, the treatment of Type I diabetes using the biological device or devices as disclosed herein should achieve this level either by providing the appropriate amount of pancreatic islet cells based on the body weight of the individual, or providing an amount of islet cells sufficient to supplement the individual's active insulin-producing pancreatic islet cells.

As mentioned hereinabove, biological device or devices comprising the amphiphilic network of the present invention are typically implanted in a diabetic individual. It is preferable that the most non-invasive technique of implantation be employed. A non-invasive technique generally refers to a procedure that creates minimal pain, discomfort and recovery time of the individual into which the device is implanted. Given the relatively small diameter and length of the biological devices of the present invention, only a minimal incision is required to implant the device. It is further envisioned that a very narrow cylindrical device, as described hereinabove, could be implanted by injection utilizing a syringe of sufficient size. It should also be appreciated that several devices can be implanted simultaneously into the body of a diabetic individual to achieve the desired cell count necessary to reverse the effects of diabetes.

GENERAL EXPERIMENTAL

The following examples are set forth to describe the amphiphlic networks of the present invention in further detail and to illustrate the methods of the present invention. However, the examples should not be construed as limiting the present invention in any manner. Throughout this specification and claims, all percentages are by weight and are based on the total amphiphilic polymer network weight unless otherwise specifically stated.

Network Synthesis

The synthesis of the three-arm star allyl-telechelic polyisobutylene $(\emptyset(PIB-MA)_3)$ was carried out by living cationic polymerization using tricumyl chloride/TiCl$_4$/N,N-dimethylacetamide/–80° C. system with end-quenching with allyltrimethylsilane. Allyl-tri-telechelic polyisobutylene was functionalized to $(\emptyset(PIB-MA)_3)$ by the method disclosed by B. Ivan, J. P. Kennedy and V. S. C. Chang, J. Polym. Sci. Polym Chem. Ed. 18, 3177 (1980). The PDMAAm-l-three-arm star polyisobutylene networks were prepared by benzoyl peroxide induced free radical copolymerization of DMAAm with $(\emptyset(PIB-MA)_3)$ of $M_n$=4,500, $M_w/M_n$=1.12; $M_n$=10,200, $M_w/M_n$=1.07; $M_n$=15,000, $M_w/M_n$=1.04, in tetrahydrofuran at 40° C. for 24 hours. Initiation was accelerated by N,N-dimethyl-p-toluidine. Polymers were extracted sequentially with hexane and methanol for 24 hours to remove unreacted $(\emptyset(PIB-MA)_3)$, DMMAmm and PDMAAm, respectively.

The amphiphilic networks of the present invention were evaluated for their ability to swell in n-heptane and distilled water. The tensile pro perties of the amphiphilic networks of the present invention were also evaluated.

Swelling Studies

Dried and preweighed disc shaped samples of the amphiphilic networks of the present invention were used for the swelling experiments. Each disc shaped sample had a diameter of 11 millimeter and a thickness of 3 millimeters. Samples were placed in either n-heptane or distilled water at room temperature (22° C.). Samples were periodically removed from the swelling media, the excess liquid was removed from the samples by blotting with tissue paper, and the samples were weighed. The swelling kinetics for each sample network was obtained by plotting the swelling time ratio Q(t). The swelling time ration, Q(t), represents the amount of solvent in grams at time (t)/gram of dry network versus time.

Figure 2A:
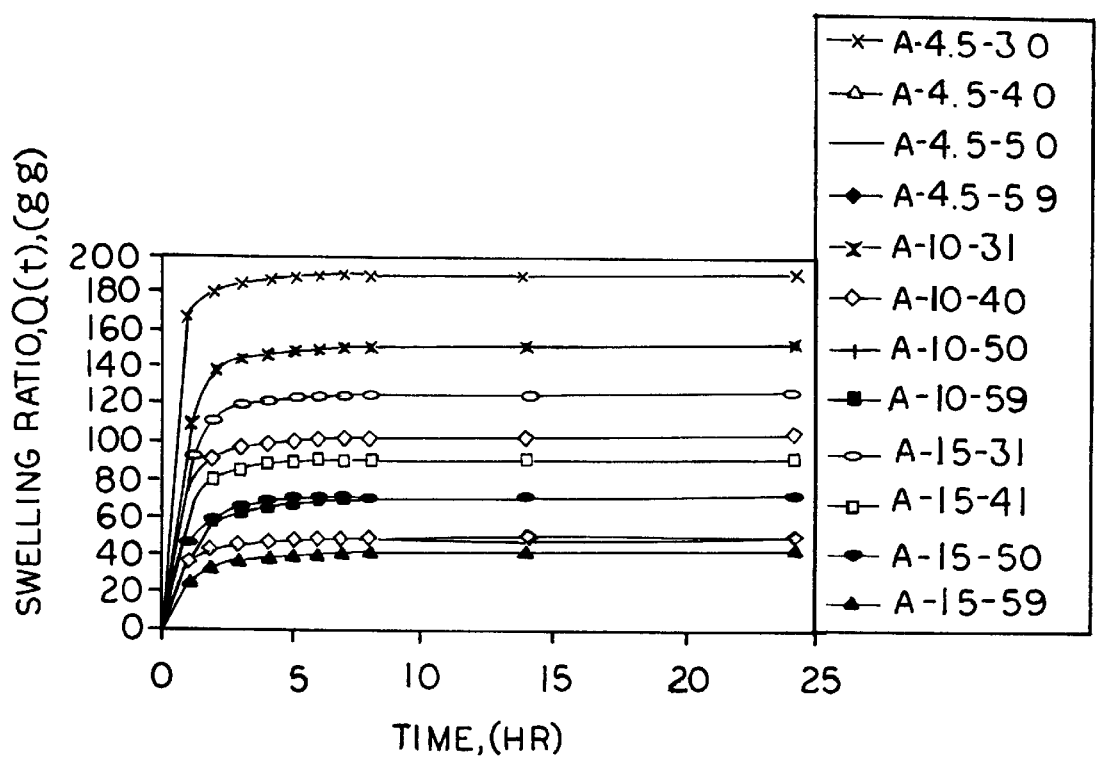
FIG. 2A is a representative graph plotting a series of swelling curves of representative amphiphilic networks of the present invention in distilled water at room temperature.
Figure 2B:
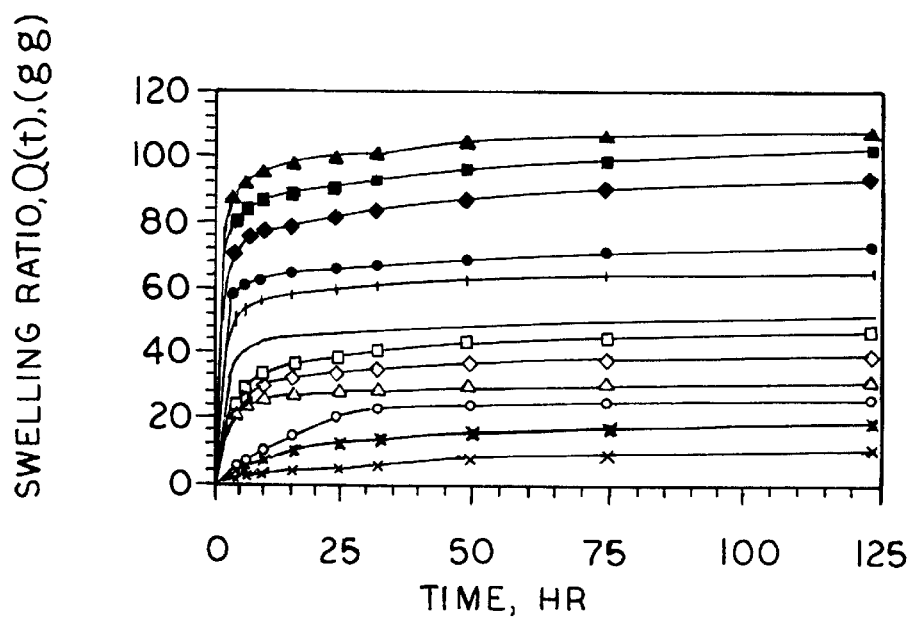
FIG. 2B is a representative graph plotting a series of swelling of representative amphiphilic networks of the present invention in n-heptane at room temperature.

FIGS. 2A and 2B show the swelling profiles of the amphiphilic polymer networks of the present invention in water and n-heptane, respectively. As shown in FIGS. 2A and 2B, swelling in water reaches equilibria in approximately 14 hours, while swelling in n-heptane does not reach equilibria until after about 72 hours. The swelling increases in n-heptane and decreases in water with increasing PIB content.

Figure 3:
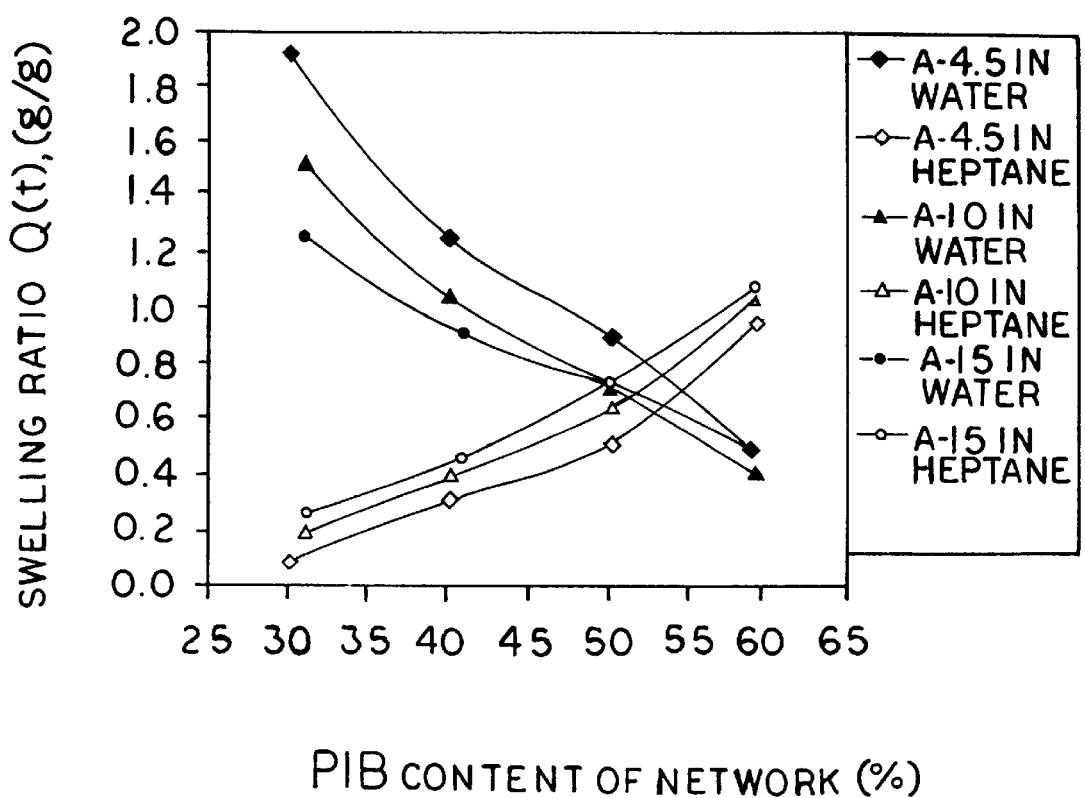
FIG. 3 is a representative graph plotting the equilibrium swelling of the amphiphilic networks of the present invention in distilled water and n-heptane.

FIG. 3 is a graph summarizing the equilibrium swelling data obtained from the swelling profiles of FIGS. 2A and 2B. As shown in FIG. 3, equilibrium swelling in n-heptane increases with increasing molecular weight of the $\emptyset$(PIB-MA)$_3$, and reaches a higher value than amphiphilic networks of the same compositions obtained using linear bifunctional polyolefins, such as linear methacrylate-capped polyisobutylene. The equilibrium swelling in water follows the opposite trend. The swelling of the amphiphilic polymer networks in water increases with decreasing PIB molecular weight.

Mechanical Properties

The mechanical properties, including stress at break (MPa) and strain at break(%), of the amphiphilic networks of the present invention were evaluated. The amphiphilic networks of the present invention were prepared in rectangular, 9×14 centimeter Teflon® molds sealed with Teflon® coated aluminum foil. The tensile properties of the amphiphilic networks of the present invention were determined by use of an Instron 5567 tensometer with a 5 kg load cell and a crosshead speed of 50 mm/minute and with a 30 mm clamp separation. The strain was measured by a video Extensometer at a calculated strain rate of 1.67/minute. According to ASTM D638-5, a minimum of three microdumbells of networks containing 50% polyisobutylene were tested, and the averages are reported. The stress at break (in MPa) and the strain at break (%) for each sample was determined and is shown in Table II hereinabelow.

TABLE II

| Example No. | Network | Type of PIB in Network | Stress at break, MPa | | Strain at break, % | |
|---|---|---|---|---|---|---|
| | | | Dry | Wet | Dry | Wet |
| 13 | A-4.5-52 | $\emptyset$(PIB-MA)$_3$ | 6.51 | 1.00 | 253 | 250 |
| 14 | A-10-53 | $\emptyset$(PIB-MA)$_3$ | 6.03 | 0.84 | 314 | 268 |
| 15 | A-15-52 | $\emptyset$(PIB-MA)$_3$ | 0.98 | 0.83 | 320 | 297 |
| Comp. 16 | A-4.5-50 | MA-PIB-MA | 16.67 | 0.46 | 113 | 116 |
| Comp. C17 | A-10-57 | MA-PIB-MA | 17.16 | 0.58 | 198 | 205 |

Example No. 13 is an amphiphilic network comprising $\emptyset$(PIB-MA)$_3$ having a molecular weight, M$_n$ of about 4,500 g/mol, and an overall hydrophilic to hydrophobic ratio of about 50:50. As Table II shows, a dry amphiphilic network of Example 13 exhibits a stress at break of 6.51 Mpa, and a strain at break of 253%. A wet amphiphilic network of Example 13 exhibits a stress at break of 1 Mpa, and a strain at break of 250%. Example 14 is an amphiphilic network comprising $\emptyset$(PIB-MA)$_3$ having a molecular weight, M$_n$, of about 10,000 g/mol, and an overall hydrophilic to hydrophobic ratio of about 50:50. As Table II indicates, a dry amphiphilic network of Example 14 exhibits a stress at break of 6.03 Mpa, and a strain at break of 314%. A wet amphiphilic network of Example 14 exhibits a stress at break of 0.84 Mpa, and a strain at break of 268%. Example No. 15 is an amphiphilic network comprising $\emptyset$(PIB-MA)$_3$ having a molecular weight, M$_n$, of about 15,000 g/mol, and an overall hydrophilic to hydrophobic ratio of about 50:50. As Table II shows, a dry amphiphilic network of Example 15 exhibits a stress at break of 0.98 Mpa, and a strain at break of 320%. A wet amphiphilic network of Example 15 exhibits a stress at break of 0.83 Mpa, and a strain at break of 297%.

Comparative Example No. 16 is an amphiphilic network comprising a linear bifunctional methacrylate-capped polyisobutylene (MA-PIB-MA) having a molecular weight, M$_n$, of about 4,500 g/mol, and an overall hydrophilic to hydrophobic ratio of about 50:50. As Table II shows, a dry amphiphilic network of Comparative Example 16 exhibits a stress at break of 16.67 MPa, and a strain at break of 113%. A wet amphiphilic network of Comparative Example 16 exhibits a stress at break of 0.46 MPa, and a strain at break of 116%. Comparative Example No. 17 is an amphiphilic network comprising a linear bifunctional methacrylate-capped polyisobutylene (MA-PIB-MA) having a molecular weight, M$_n$, of about 10,000 g/mol, and an overall hydrophilic to hydrophobic ratio of about 50:50. As Table II shows, a dry amphiphilic network of Comparative Example 17 exhibits a stress at break of 17.16 MPa, and a strain at break of 198%. A wet amphiphilic network of Comparative Example 17 exhibits a stress at break of 0.58 MPa, and a strain at break of 205%.

The tensile strengths of dry amphiphilic networks based on $\emptyset$(PIB-MA)$_3$ decrease and elongations increases with increasing M$_n$ of the PIB crosslinker, due to the decreasing crosslink densities. Water-swollen (wet) amphiphilic networks based on $\emptyset$(PIB-MA)$_3$ exhibit higher tensile strengths and higher elongations of the same M$_n$PIB than those networks prepared from linear MA-PIB-MA.

Figure 4:
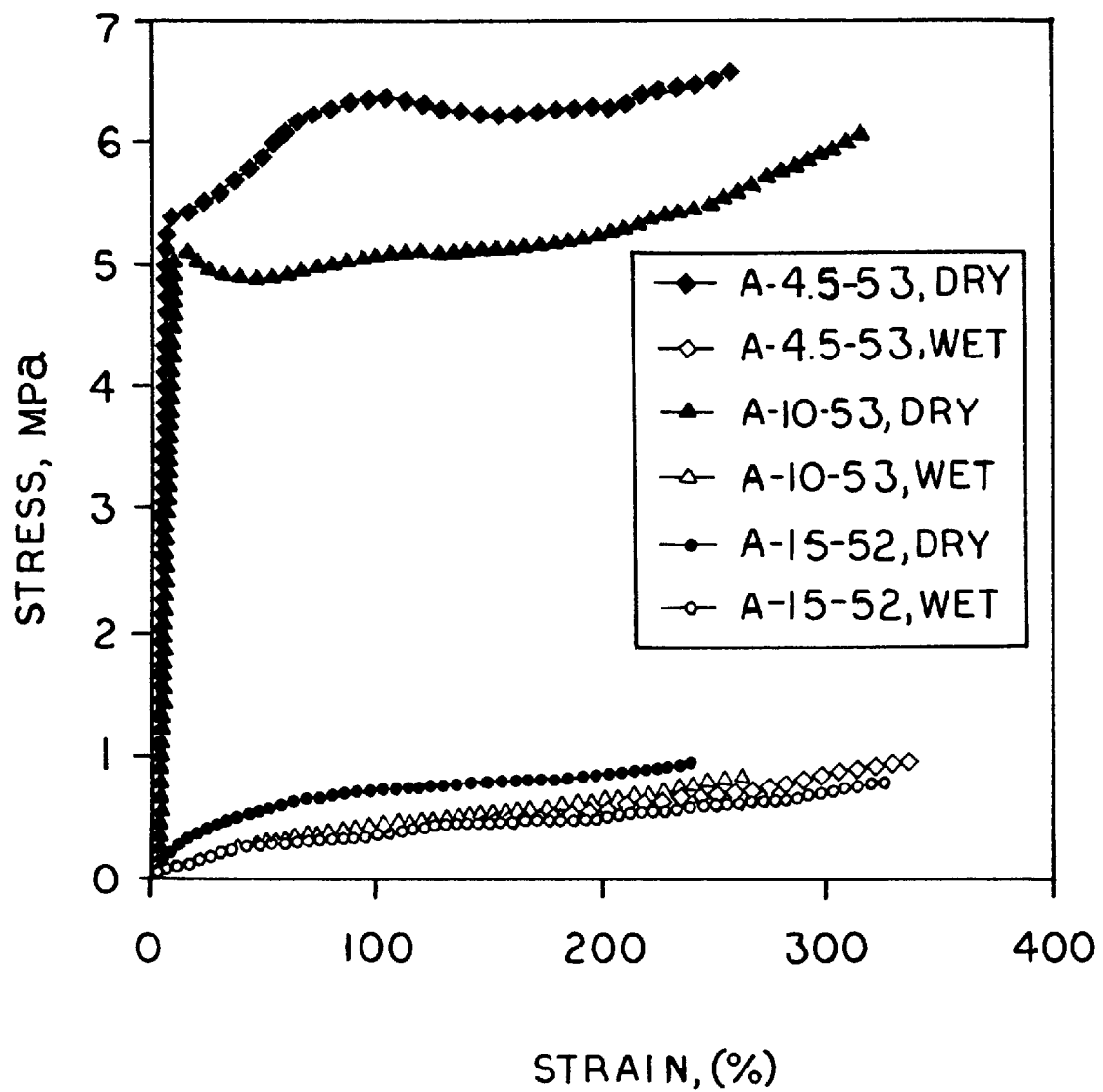
FIG. 4 is a representative graph plotting the stress-strain curves of wet and dry amphiphilic networks of the present invention.

FIG. 4 shows the stress-strain properties of a series of wet and dry amphiphilic networks of the present invention comprising hydrophilic PDMAAm that have been crosslinked with different molecular weight $\emptyset$(PIB-MA)$_3$, namely a M$_n$ of 4,500; 10,200; and 15,00 g/mol, and having substantially that same overall ratio of hydrophilic monomer to hydrophobic monomer in the network.

Based on the foregoing disclosure, it is therefore demonstrated that the objects of the present invention are accomplished by the amphiphilic polymer networks and methods of preparation disclosed. The amphiphilic polymer networks of the present invention are particularly well suited as implantable biological devices. It is further demonstrated that the present invention provides an amphiphilic network that has improved immunoisolatory and mechanical properties as compared to amphiphilic networks of the prior art. It should be understood that the selection of specific hydrophobic crosslinker and hydrophilic monomers and biologically active moieties can be determined by one having ordinary skill in the art without departing from the spirit of the invention herein disclosed and described. It should therefore be appreciated that the present invention is not limited to the specific embodiments described above, but includes variations, modifications and equivalent embodiments defined by the following claims.

We claim:

1. An amphiphilic network comprising the reaction product of hydrophobic crosslinking agents and hydrophilic monomers, wherein the hydrophobic crosslinking agents are telechelic three-arm polyisobutylenes, having acrylate or methacrylate end caps represented by formula (I);

(I)

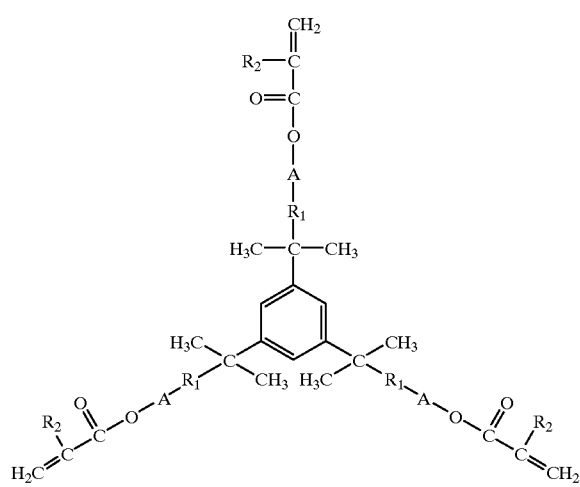

wherein $R_1$ is an isobutylene polymer represented by formula (II):

(II)

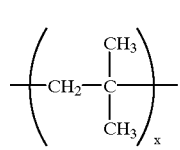

wherein A is a moiety that connects $R_1$ to the acrylate or methacrylate end caps;

wherein $R_2$ is hydrogen or a methyl group;

wherein x is the degree of polymerization of the isobutylene; and wherein said hydrophilic monomers are derived from an acrylate selected from the group consisting of formulas (III), (IV) and (V):

(III)

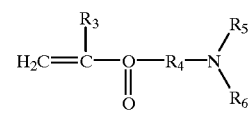

(IV)

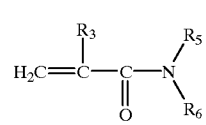

(V)

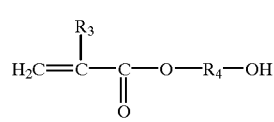

wherein $R_3$ is hydrogen or methyl, $R_4$ is an alkylene group having from about 2 to about 4 carbon atoms, and $R_5$ and $R_6$ may be the same or different and each is hydrogen or an alkyl radical having 1 to about 4 carbon atoms.

2. The amphiphilic network of claim 1, wherein A is at least one of:

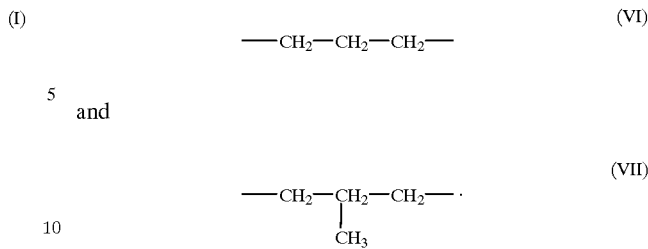

3. The amphiphilic network of claim 1, wherein the $M_n$ of the hydrophobic crosslinking agent is from about 2,000 g/mol to about 15,000 g/mol.

4. The amphiphilic network of claim 3, wherein the $M_n$ of the hydrophobic crosslinking agent is about 4,500 g/mol.

5. The amphiphilic network of claim 3, wherein the $M_n$ of the hydrophobic crosslinking agent is about 10,000 g/mol.

6. The amphiphilic network of claim 3, wherein the $M_n$ of the hydrophobic crosslinking agent is about 15,000 g/mol.

7. The amphiphilic network of claim 1, wherein the ratio of the hydrophobic crosslinking agent to the hydrophilic monomer is from about 80:20 to about 20:80 by weight.

8. The amphiphilic network of claim 7, wherein the ratio of the hydrophobic crosslinking agent to the hydrophilic monomer is from about 70:30 to about 30:70 by weight.

9. The amphiphilic network of claim 7, wherein the ratio of the hydrophobic crosslinking agent to the hydrophilic monomer is from about 60:40 to about 40:60 by weight.

10. The amphiphilic network of claim 7, wherein the ratio of the hydrophobic crosslinking agent to the hydrophilic monomer is from about 50:50 by weight.

11. The amphiphilic network of claim 1, wherein the network can absorb water.

12. The amphiphilic network of claim 1, wherein the network can absorb n-heptane.

13. The amphiphilic network of claim 1, wherein the network has a tensile strength as measured by the stress at break of at least about 0.8 MPa.

14. The amphiphilic network of claim 1, wherein the network has an elongation of at least about 250 percent.

15. A method of forming an amphiphilic network comprising the steps of:

copolymerizing and crosslinking hydrophilic monomers, wherein said hydrophilic monomers are derived from an acrylate selected from the group consisting of formulas (III), (IV) and (V):

(III)

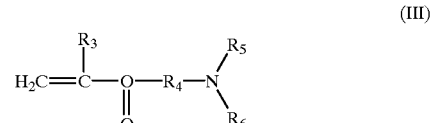

(IV)

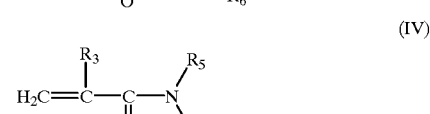

(V)

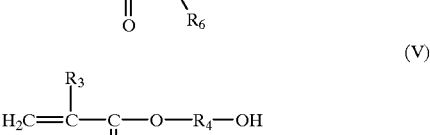

wherein $R_3$ is hydrogen or methyl, $R_4$ is an alkylene group having from about 2 to about 4 carbon atoms, and $R_5$ and $R_6$ may be the same or different and each is hydrogen or an alkyl radical having 1 to about 4 carbon atoms;

with hydrophobic crosslinking agents, wherein the hydrophobic crosslinking agents are acrylate or methacrylate-capped three-arm star polyisobutylenes represented by formula (I):

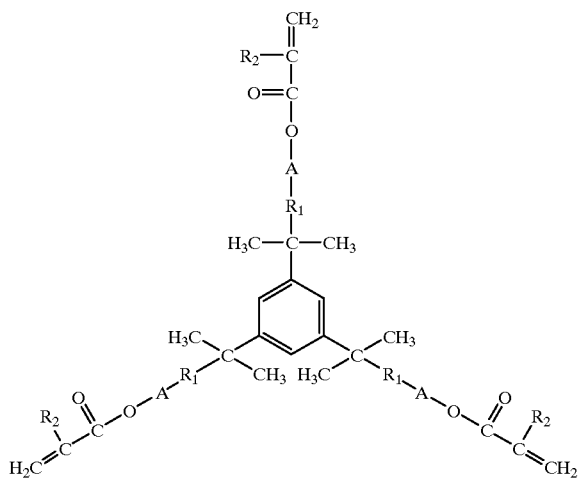

(I)

wherein $R_1$ is an isobutylene polymer represented by formula (II):

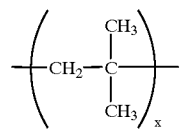

(II)

wherein A is a moiety that connects $R_1$ to the acrylate or methacrylate end caps;

wherein $R_2$ is hydrogen or a methyl group; and wherein x is the degree of polymerization of the isobutylene.

16. The method of claim 15, wherein A is at least one of:

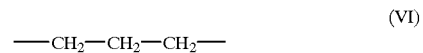

(VI)

and

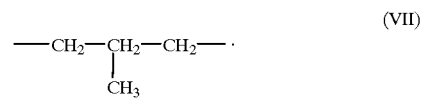

(VII)

17. The method of claim 16, wherein said amphiphilic polymer network is copolymerized and simultaneously crosslinked in a horizontally-disposed and rotating cylinder.

* * * * *

UNITED STATES PATENT AND TRADEMARK OFFICE
CERTIFICATE OF CORRECTION

PATENT NO.   : 6,365,171 B1
DATED        : April 2, 2002
INVENTOR(S)  : Joseph P. Kennedy et al.

It is certified that error appears in the above-identified patent and that said Letters Patent is hereby corrected as shown below:

Column 12,
Lines 40-45, the equation 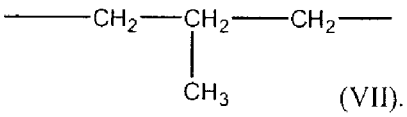 (VII).

should be 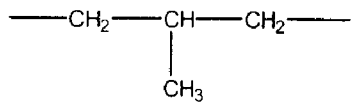

(VII).

Column 22,
Line 9, the equation 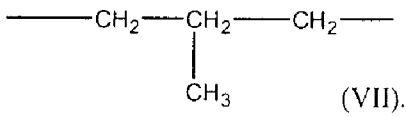 (VII).

should be 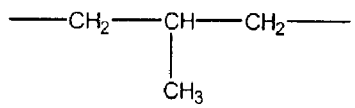

(VII).

Column 24,
Line 24, the equation 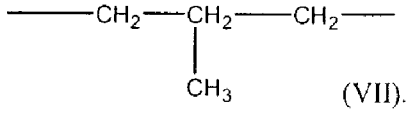 (VII).

should be 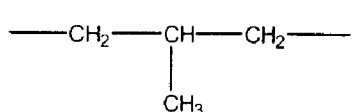

(VII).

Signed and Sealed this

Fourth Day of February, 2003

JAMES E. ROGAN
*Director of the United States Patent and Trademark Office*